(12) United States Patent
Jeon et al.

(10) Patent No.: US 9,757,482 B2
(45) Date of Patent: Sep. 12, 2017

(54) IRON OXIDE NANOCAPSULES, METHOD OF MANUFACTURING THE SAME, AND MRI CONTRAST AGENT USING THE SAME

(75) Inventors: Bong-Sik Jeon, Daejeon (KR); Eung Gyu Kim, Daejeon (KR); Eun Byul Kwon, Daejeon (KR); Ju Young Park, Daejeon (KR); Wan Jae Myeong, Daejeon (KR)

(73) Assignee: HANWHA CHEMICAL CORPORATION, Seoul (KR)

( * ) Notice: Subject to any disclaimer, the term of this patent is extended or adjusted under 35 U.S.C. 154(b) by 1060 days.

(21) Appl. No.: 13/819,525

(22) PCT Filed: Aug. 30, 2011

(86) PCT No.: PCT/KR2011/006396
§ 371 (c)(1),
(2), (4) Date: Feb. 27, 2013

(87) PCT Pub. No.: WO2012/030134
PCT Pub. Date: Mar. 8, 2012

(65) Prior Publication Data
US 2013/0164223 A1  Jun. 27, 2013

(30) Foreign Application Priority Data

Aug. 30, 2010 (KR) .................. 10-2010-0084061

(51) Int. Cl.
*A61K 49/18* (2006.01)
(52) U.S. Cl.
CPC ...... *A61K 49/1893* (2013.01); *A61K 49/1824* (2013.01); *A61K 49/1827* (2013.01); *A61K 49/1857* (2013.01); *A61K 49/1887* (2013.01)
(58) Field of Classification Search
CPC ............ A61K 49/1839; A61K 49/1857; A61K 49/1824; A61K 49/1827; A61K 49/1887
See application file for complete search history.

(56) References Cited

U.S. PATENT DOCUMENTS

2003/0146529 A1* 8/2003 Chen .................. B01J 13/06
264/4.1
2006/0222594 A1 10/2006 Lee et al.

FOREIGN PATENT DOCUMENTS

| KR | 10-2001-0031289 | 4/2001 |
| KR | 10-2004-0092969 | 11/2004 |
| KR | 10-2006-0084702 | 7/2006 |
| KR | 10-2009-0085834 | 8/2009 |
| KR | 1020090085834 | 10/2009 |
| WO | 2006/028129 | 3/2006 |

OTHER PUBLICATIONS

Okassa et al., European J. of Pharma and Biopharma 67 (2007), 31-38.*
International Search Report of corresponding application No. PCT/KR2011/006396 mailed May 1, 2012.
Bong-sik Jeon, et al., "Controlled Aggregated of Magnetite Nanoparticles for Highly Sensitive MR Contrast Agent," Journal of Nanoscience and Nanotechnology, vol. 9, pp. 7118-7122, Seoul, South Korea, 2009.
European Office Action of corresponding European application No. 11822109.2, dated Jun. 2, 2016.
Astete et al: "Size control of poly(d,1-lactide-co-glycolide) and poly (d,1-lactide-co-glycolide)-magnetite nanoparticles synthesized by emulsion evaporation technique", Colloids and Surfaces. A, Physicachemical and Engineering Aspects, Elsevier, Amsterdam, NL, vol. 299, No. 1-3, Mar. 23, 2007 (Mar. 23, 2007), pp. 209-216, XP005935472, ISSN: 0927-7757.
Patel et al: o;Poiy(d,i-lactide-co-giycolide) coated superparamagnetic iron oxide nanoparticles: Synthesis, pharacterization and in vivo study as MRI contrast agent, Colloids and Surfaces. A, Physicachemical and Engineering Aspects, Elsevier, Amsterdam, NL, vol. 313-314, Dec. 27, 2007 (Dec. 27, 2007), pp. 91-94, XP022402227, ISSN: 0927-7757.

* cited by examiner

Primary Examiner — Robert Cabral
(74) Attorney, Agent, or Firm — Hauptman Ham, LLP

(57) ABSTRACT

Provided are iron oxide nanocapsules for an MRI contrast agent having high contrast, in which a plurality of iron oxide nanoparticles having a hydrophobic ligand attached thereto are encapsulated in an encapsulation material including a biodegradable polymer and a surfactant, and which satisfy Relations 1, 2, 3, 4 and 5 below. Also a method of manufacturing the iron oxide nanocapsules is provided.

| $5 \leq 100 * D_\mu(IO)/C_\omega^-(IO)$ | [Relation 1] |
| $2.5 \leq 100 * D_\mu(Cap)/C_\omega^-(Cap)$ | [Relation 2] |
| $0.5 \text{ wt \%} \leq F(IO) \leq 50 \text{ wt \%}$ | [Relation 3] |
| $1 \text{ nm} \leq D_\mu(IO) \leq 25 \text{ nm}$ | [Relation 4] |
| $50 \text{ nm} \leq D_\mu(Cap) \leq 200 \text{ nm}$ | [Relation 5] |

9 Claims, 13 Drawing Sheets

[Figure 1]
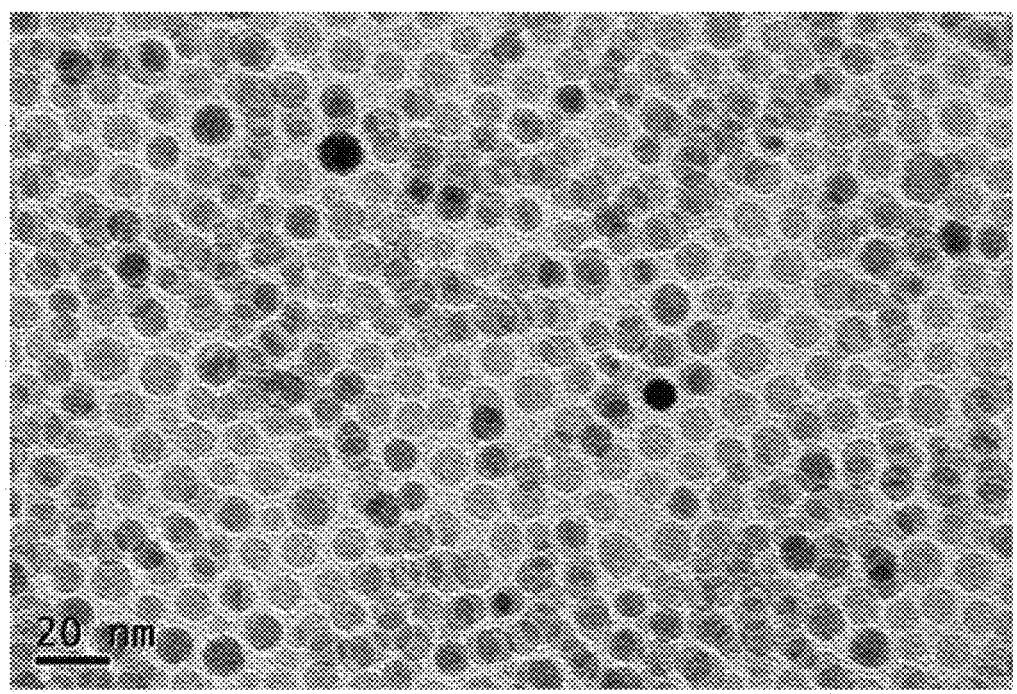

[Figure 2]
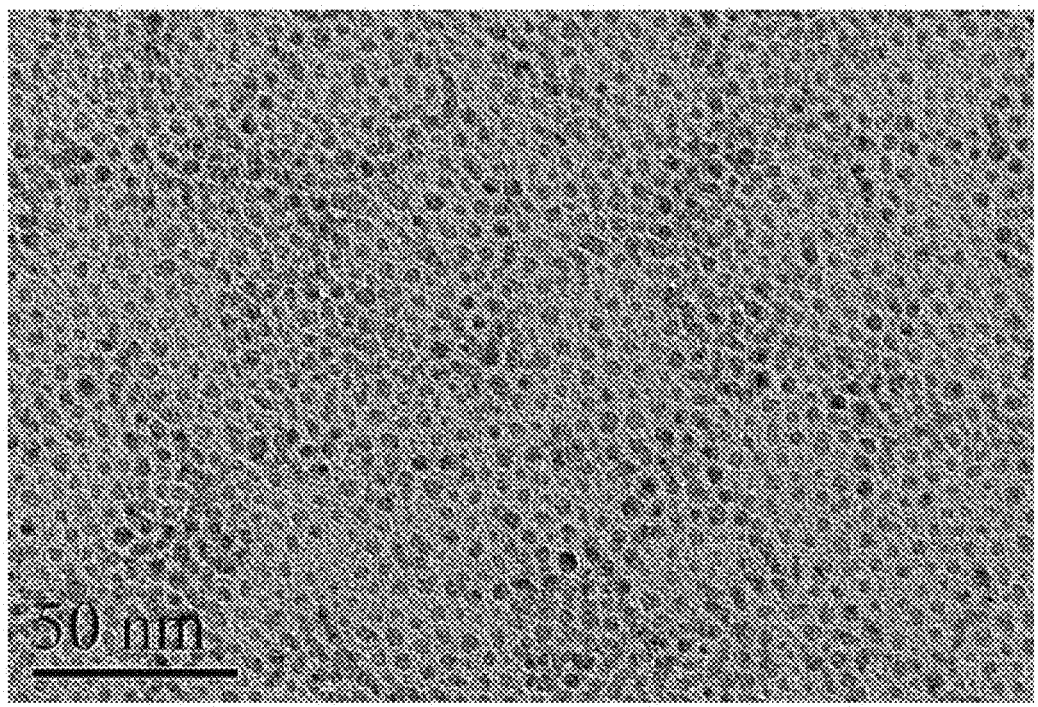

[Figure 3]
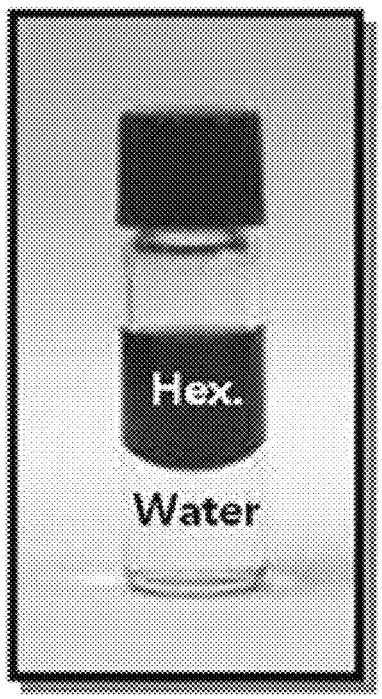
Iron Oxide NPs
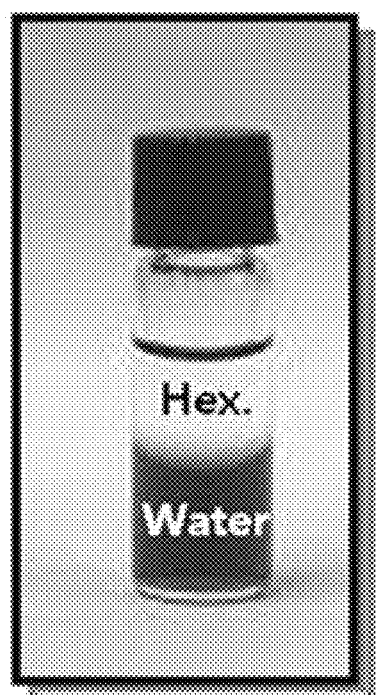
Encapsulated
Iron Oxide NPs

【Figure 4】
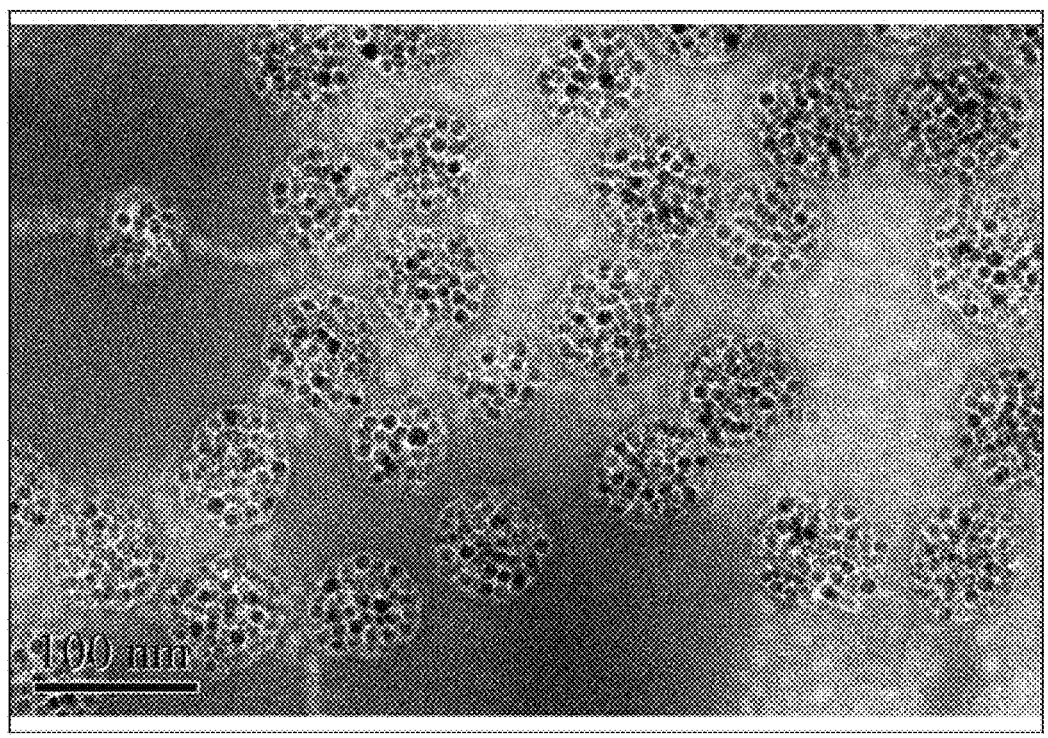

[Figure 5]
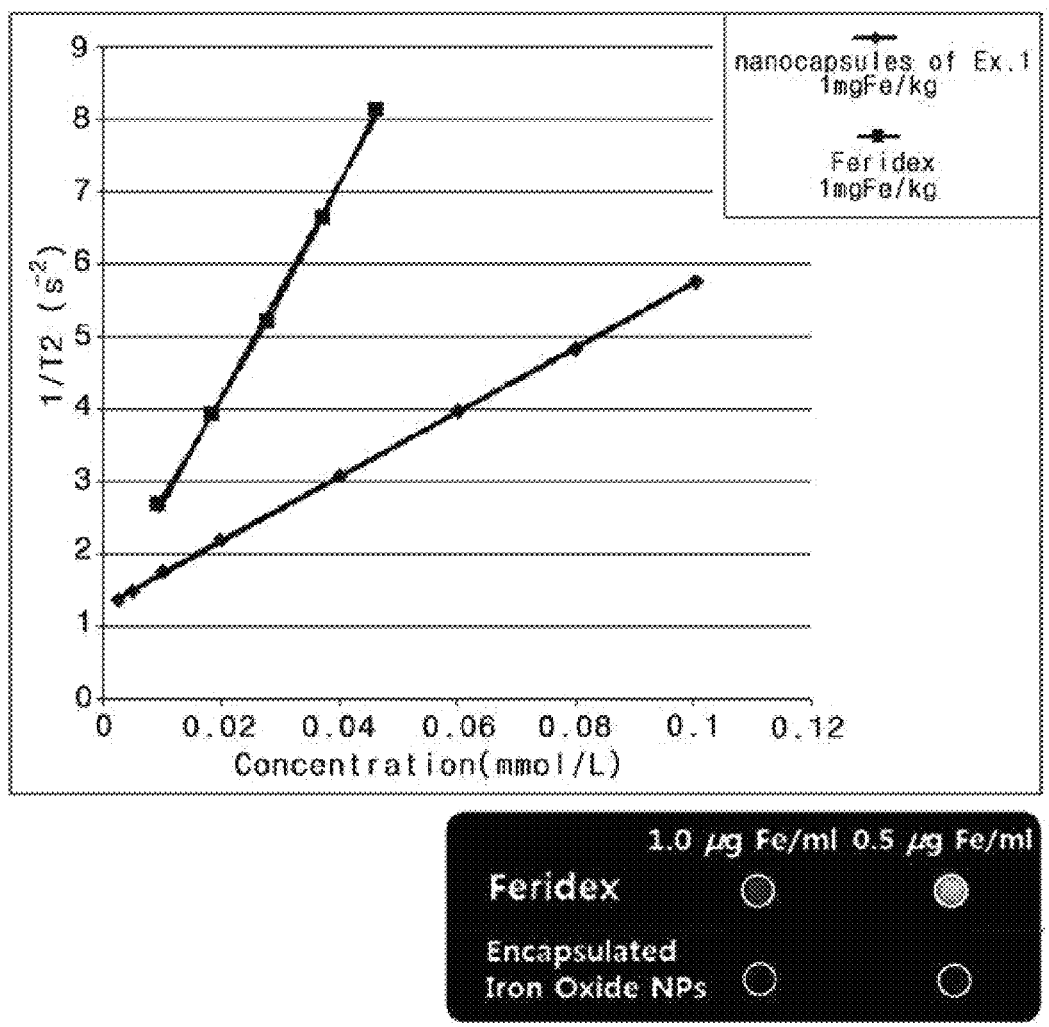

[Figure 6]
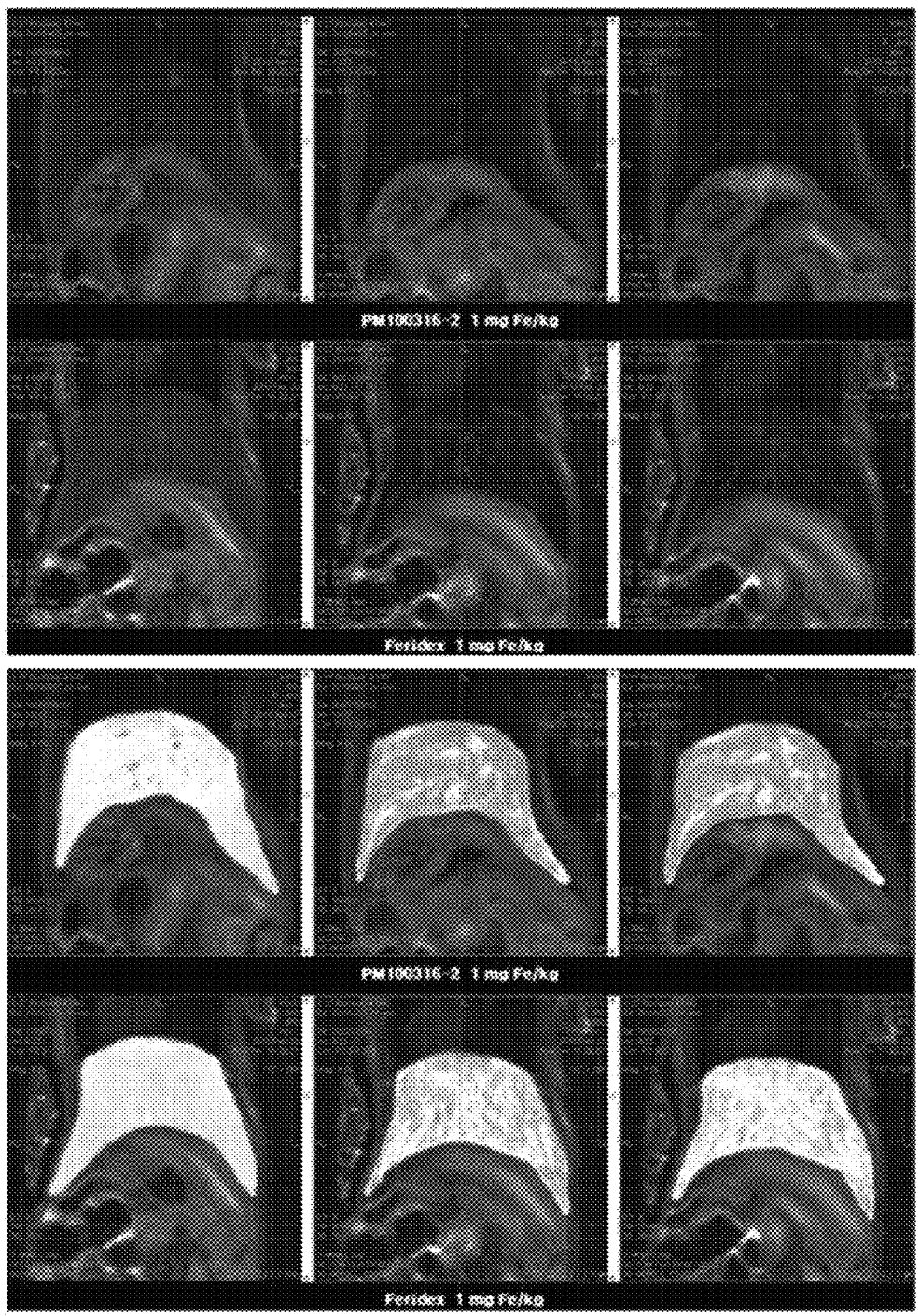

[Figure 7]
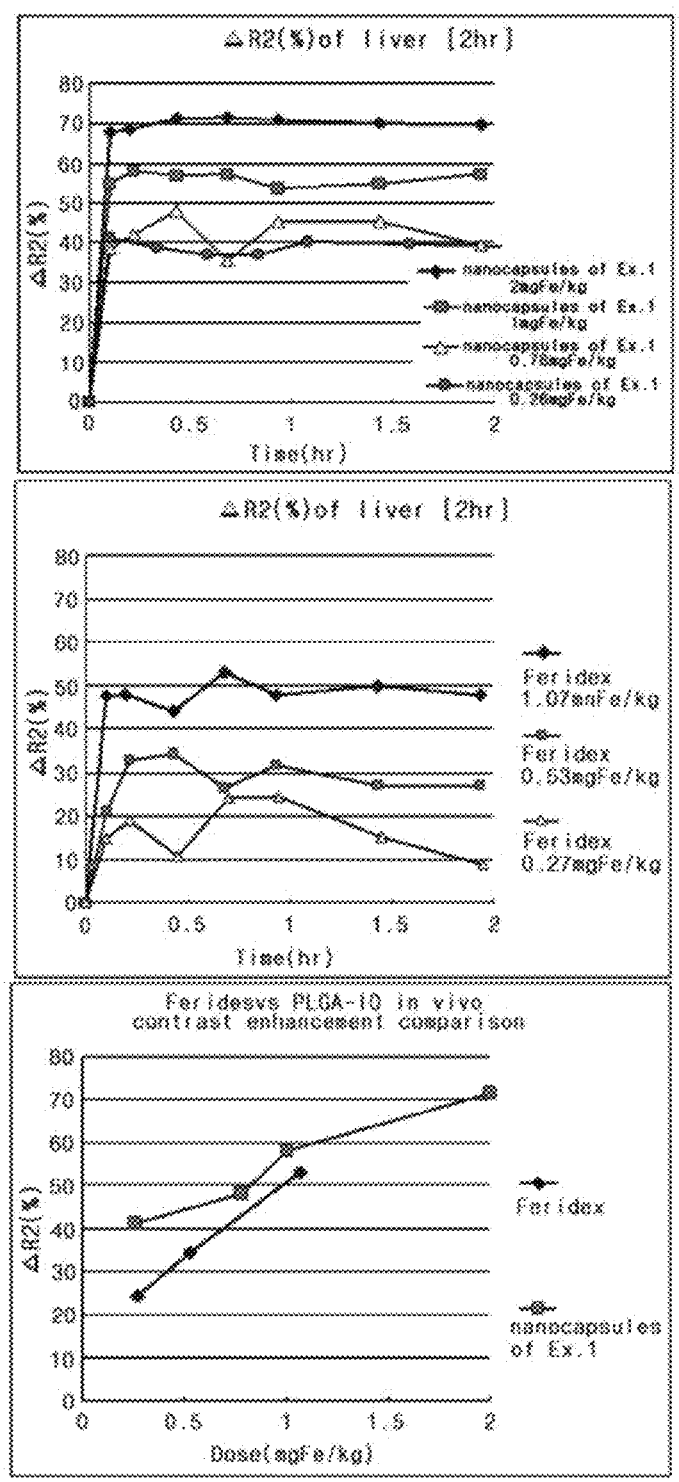

[Figure 8]
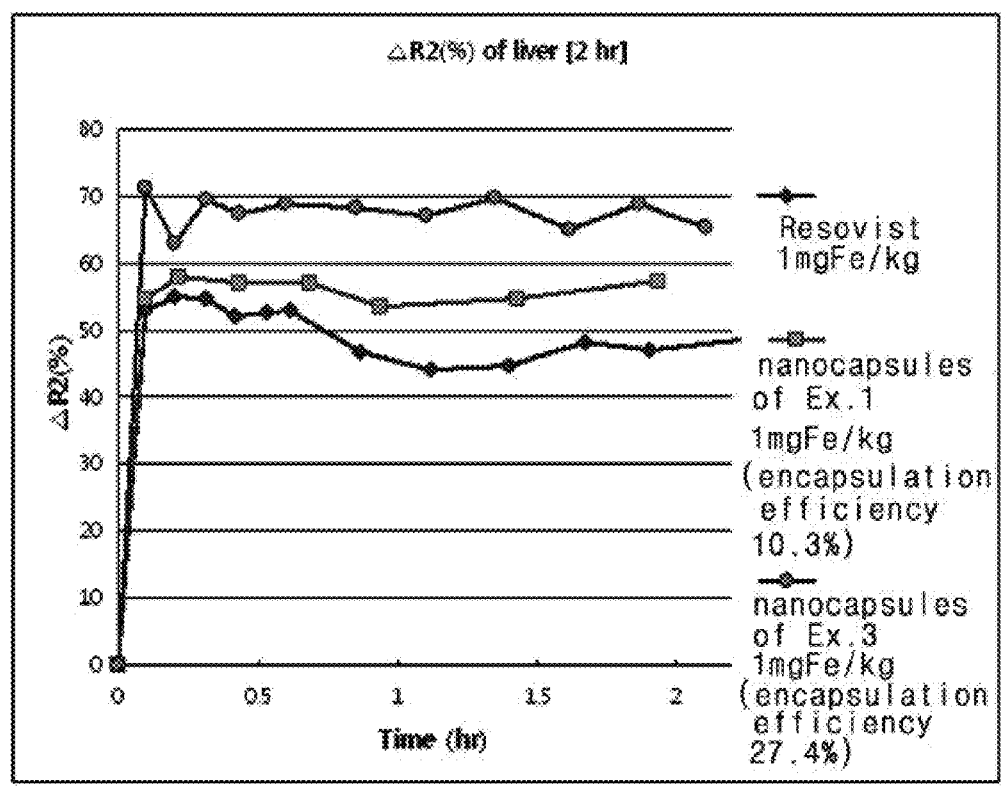

[Figure 9]
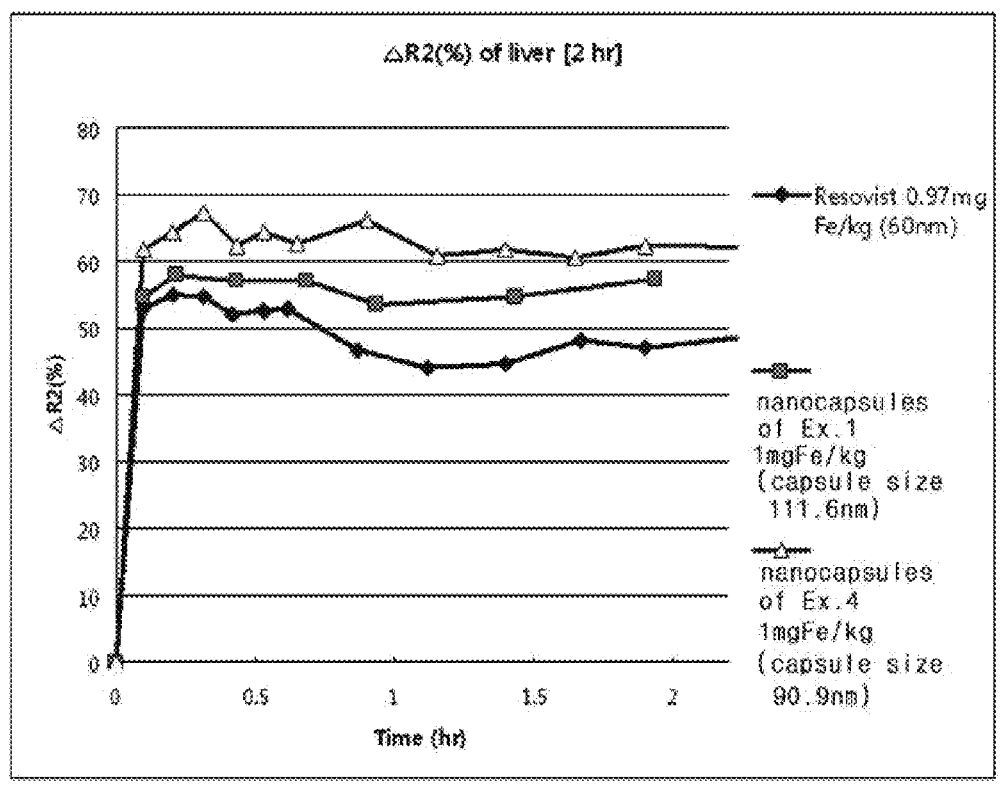

[Figure 10]
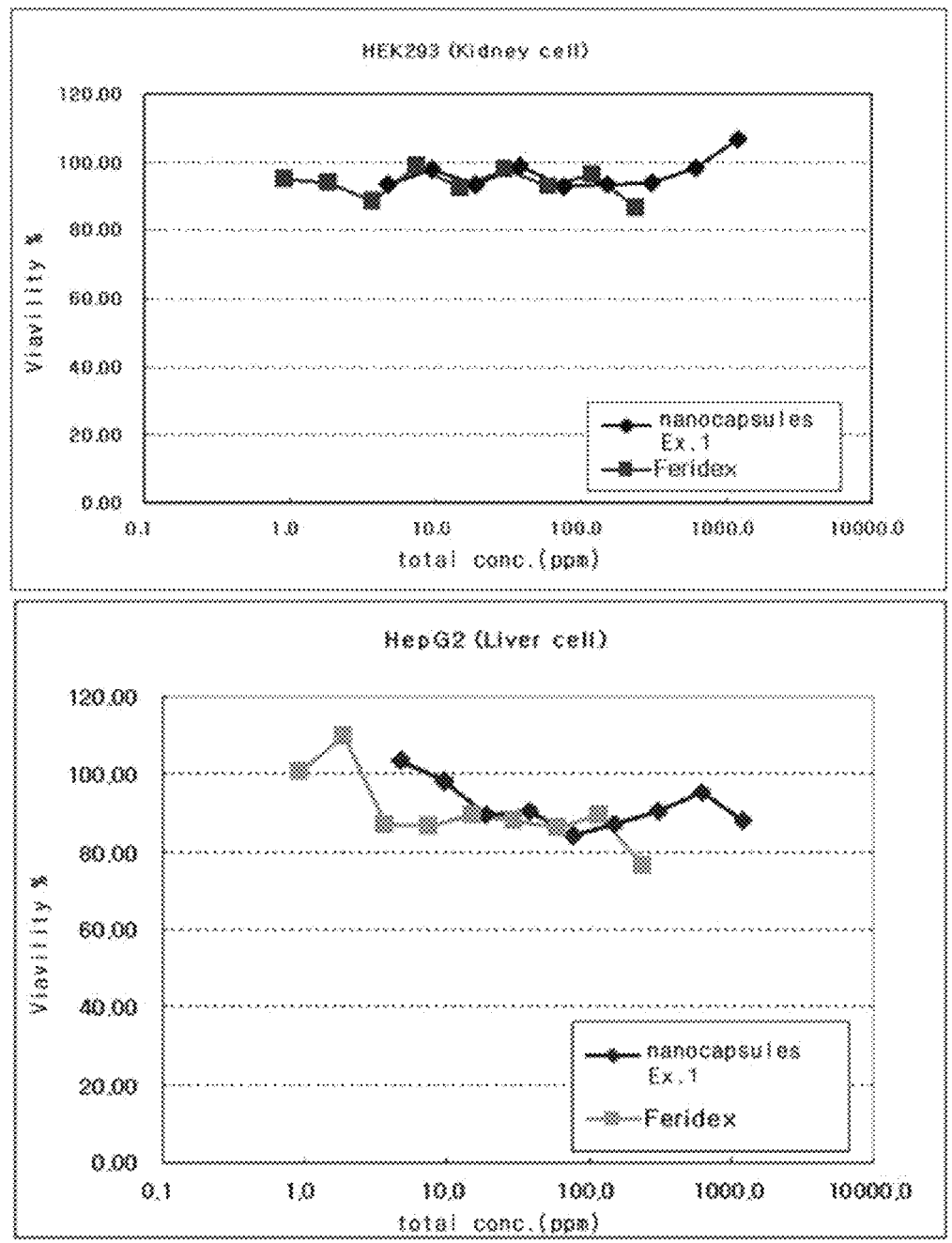

[Figure 11]
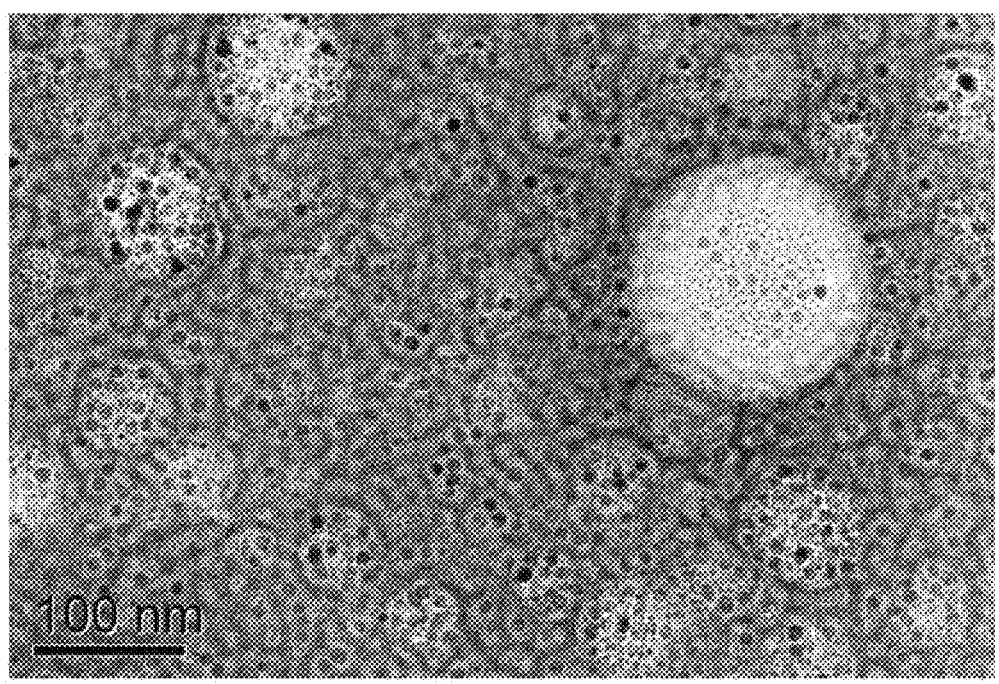

[Figure 12]
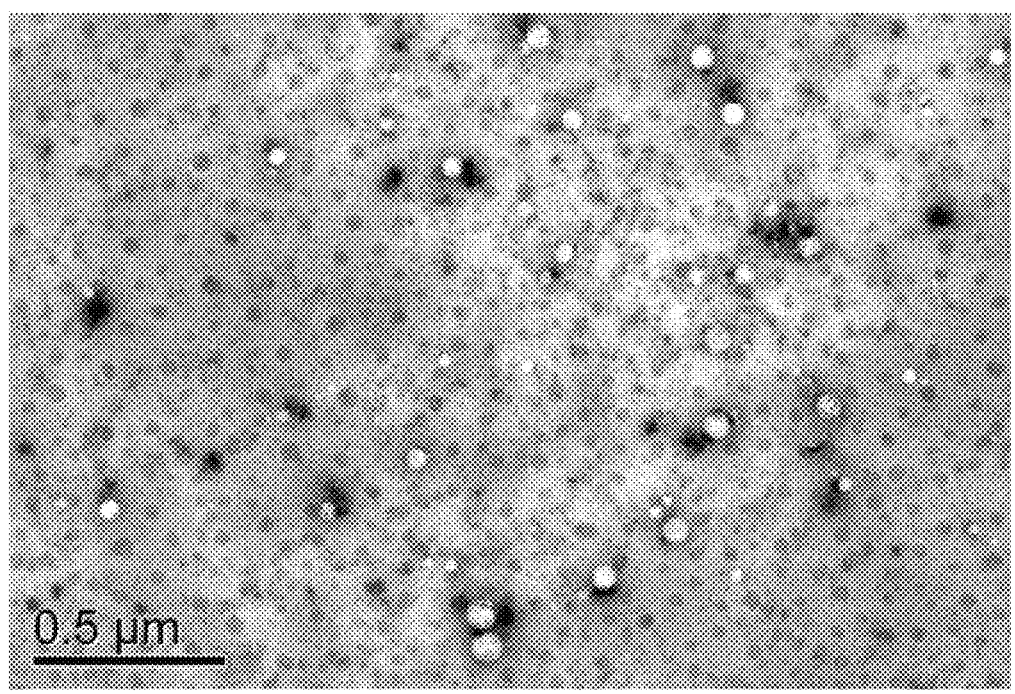

【Figure 13】
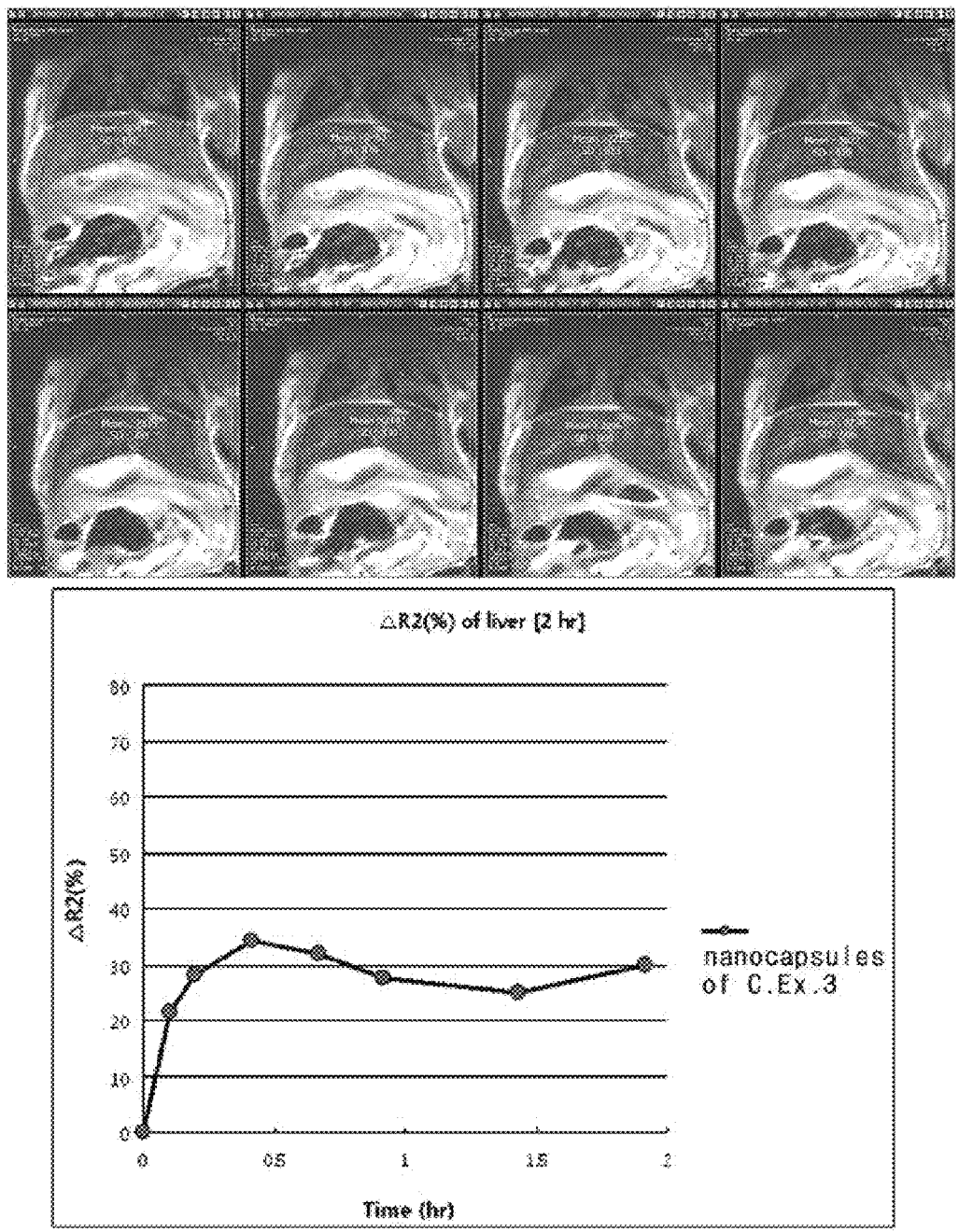

IRON OXIDE NANOCAPSULES, METHOD OF MANUFACTURING THE SAME, AND MRI CONTRAST AGENT USING THE SAME

TECHNICAL FIELD

The present invention relates to iron oxide nanocapsules for an MRI (Magnetic Resonance Imaging) contrast agent having superior contrast and a method of manufacturing the same, and more particularly, to iron oxide nanocapsules for an MRI contrast agent, which have appropriate residence time in vivo and superior contrast even when used in a small amount, and are easily functionalized, and to a method of manufacturing the same.

BACKGROUND ART

Super-paramagnetic nanoparticles are applicable in a variety of nano-bio fields including, in particular, MRI contrast agents, cell separation, hyperthermia, drug delivery, biosensors, etc., and are receiving a great amount of attention.

Methods of synthesizing super-paramagnetic nanoparticles include coprecipitation, hydrothermal synthesis, thermal decomposition, etc. Among these, coprecipitation and hydrothermal synthesis enable iron oxide nanoparticles to be easily manufactured by directly reacting iron (II) chloride and iron (III) chloride in an aqueous phase to precipitate them, but are problematic because the size of the nanoparticles is difficult to control. PCT/KR2005/004009 by Taeghwan Hyeon et al. discloses a thermal decomposition method in which a large amount of uniform nanoparticles are synthesized from a non-toxic metal salt, without size-selection procedure. However, this method is difficult to apply to bio fields because the nanoparticles having oleate attached to the surface thereof are difficult to disperse in an aqueous phase.

Methods of dispersing metal oxide nanoparticles having a hydrophobic ligand attached thereto in an aqueous phase include ligand exchange, preparation of self-assembled nanoparticles using an amphiphilic material, encapsulation using a polymer, etc.

Typically exemplified by Feridex available from AMAG or Resovist available from Bayer-Schering, a conventional commercially available liver-specific contrast agent comprising super-paramagnetic nanoparticles is manufactured using coprecipitation, but has problems in that it is difficult to control the size of iron oxide nanoparticles that exhibit contrast enhancement and the size distribution is not uniform, undesirably making it difficult to increase the contrast of the contrast agent. Furthermore, it is not easy to adjust the shape and the size of capsules having iron oxide encapsulated therein, making it difficult to regulate the biodistribution upon intravenous injection.

Korean Patent No. 10-2006-0021536 by Cheon Jin-Woo et al. discloses a technique for manufacturing water-soluble nanoparticles in which iron oxide nanoparticles synthesized using thermal decomposition are stabilized with a multifunctional ligand. According to this method, the ligand comprising an adhesive region, a cross-linking region, and an reactive region is exchanged with oleate to individually coat the iron oxide nanoparticles, and thus the size of the nanoparticles is difficult to control as required to adapt them to a liver-specific contrast agent and the aggregation effects of iron oxide nanoparticles that increase T2 relaxivity cannot be expected.

Korean Patent No. 0819377 by Ham Seung-Joo et al. discloses the use of nanoparticles synthesized via thermal decomposition as a contrast agent by dispersing them in water using an amphiphilic compound. This method collects the magnetic nanoparticles with the amphiphilic compound having hydrophobic-hydrophilic portions and thus the material is limited to the amphiphilic compound, and the size of nanoparticles, size distribution, encapsulation efficiency of iron oxide nanoparticles, etc., required as the contrast agent, are difficult to control, making it difficult to enhance T2 relaxation.

Poly(lactide-co-glycolide) (PLGA) which is a copolymer of lactic acid and glycolic acid is a material approved as an injectable material by the FDA thanks to excellent biocompatibility and biodegradability, and has recently been adopted to a variety of drug delivery fields and medical applications. PLGA causes hydrolysis with surrounding water molecules and thus decomposes with breaking an ester linkage, and thereby is decomposed within ones of months and easily eliminated from a living body.

The present invention pertains to an MRI contrast agent for diagnosing a liver in high contrast, and more particularly to a method of encapsulating iron oxide nanoparticles coated with oleic acid using a biodegradable polymer to have a uniform size and the use thereof as an liver-specific contrast agent for MRI.

KR0702671 filed in 2005 by the professor Kim Jong-Duk of KAIST discloses a method of encapsulating iron oxide nanoparticles via an emulsification-diffusion method using a biodegradable polymer such as PLA, PGA, PLGA or the like, in which iron oxide nanoparticles resulting from coprecipitation are adopted. Hence, the iron oxide nanoparticles are provided in the form of oleate not being attached to the surface thereof, and a different encapsulation method is applied thereto. Also, in the case where the maximum encapsulation efficiency exceeds 5 wt %, the size of capsules increases due to aggregation of nanoparticles, and cannot be adjusted.

A paper (J. Nanosci. Nanotechnol., 9, 7118-7122 (2009)) published in 2009 by B. S. Jeon et al. discloses a method of maintaining the size of nanoparticles while increasing the encapsulation efficiency of emulsification-diffusion method by using oleic acid, dodecanoic acid, octanoic acid or the like as an organic acid that attaches itself to the surface of nanoparticles, but the maximum encapsulation efficiency is limited to 7 wt %.

As mentioned above, commercially available liver-specific contrast agents use super-paramagnetic iron oxide nanoparticles synthesized by coprecipitation technique, and iron oxide nanoparticles recently synthesized by thermal decomposition have high crystallinity and uniformity and thus may exhibit high magnetization and high MR contrast enhancement; however, in the manufacturing process, these nanoparticles having hydrophobic oleate attached to the surface thereof are difficult to disperse in an aqueous solution, making it difficult to adopt them to bio biomedical applications.

Particularly in research into biomedical applications, because pharmacokinetics of an intravenous injection of nanoparticles may greatly vary depending on physical and chemical properties such as overall particle size, size distribution, zeta potential, density, etc., there is a need for techniques that accurately adjust these as desired.

In order to disperse the iron oxide nanoparticles having oleate attached thereto in an aqueous solution, various methods using ligand exchange or using polymeric micelles, liposomes, dendrimers, etc. by means of an amphiphilic material are under study, but MR contrast enhancement is not sufficient and the particle size is difficult to control, and thus pharmacokinetics of particles becomes inconsistent.

Also the dispersion of iron oxide nanoparticles may include for example an emulsification-diffusion method, in which when two immiscible phases (O/W) are forcibly emulsified and the organic solvent diffuses into the water phase due to a difference in concentration, an active material and a polymer dissolved in the organic solvent are diffused together, thus forming polymer capsules. However, this method is disadvantageous in terms of low encapsulation efficiency because it is difficult to disperse the iron oxide nanoparticles having oleate attached thereto in a partially water-miscible solvent.

In particular, in the case where the encapsulation efficiency is lower than 0.5 wt %, the preparation of a 1 mg Fe/ml contrast agent requires a concentration of 200 mg capsule/ml or more. As the osmotic pressure and the viscosity of an injection solution are higher, the injection may cause pain, or in severe cases, osmotic shock may ensue.

Furthermore, upon injection into a living body, microcapsules larger than nanocapsules may block capillary vessels undesirably causing side effects such as necrosis. Hence, it is very important to control the uniformity of nanocapsules.

SUMMARY OF INVENTION

Technical Problem

Therefore, the present invention has been made keeping in mind the problems encountered in the related art and an object of the present invention is to provide iron oxide nanocapsules having a small size and being very uniform with a high encapsulation efficiency by solving low encapsulation efficiency problems of a conventional emulsification-diffusion method and also to provide a method of manufacturing the same, and particularly iron oxide nanocapsules which have very high stability in an aqueous solution, reproducibly controllable absorption and distribution to tissues, and very high MRI contrast enhancement at low concentration, and prevent side effects in vivo thus exhibiting high safety, a method of manufacturing the same, and an MRI contrast agent containing such iron oxide nanocapsules.

Technical Solution

Provided are iron oxide nanocapsules, a method of manufacturing the same, and a contrast agent using the same. As such, the technical and scientific terms used should be interpreted as having meanings typically understood by those skilled in the art unless other definitions are presented. Moreover, descriptions of known functions and constructions, even if they are pertinent to the present invention, are regarded as unnecessary and may be omitted when they would make the characteristics of the invention unclear.

In one aspect, the present invention provides iron oxide nanocapsules in which a plurality of iron oxide nanoparticles having a hydrophobic ligand attached thereto are encapsulated in an encapsulation material including a biodegradable polymer and a surfactant, and which satisfy Relations 1, 2, 3, 4 and 5 below.

$5 \leq 100 \cdot D_\mu(IO)/C_{\overline{\omega}}(IO)$ [Relation 1]

$2.5 \leq 100 \cdot D_\mu(Cap)/C_{\overline{\omega}}(Cap)$ [Relation 2]

$0.5 \text{ wt \%} \leq F(IO) \leq 50 \text{ wt \%}$ [Relation 3]

$1 \text{ nm} \leq D_\mu(IO) \leq 25 \text{ nm}$ [Relation 4]

$50 \text{ nm} \leq D_\mu(Cap) \leq 200 \text{ nm}$ [Relation 5]

(in Relation 1, $D_\mu(IO)$ is the average size of iron oxide nanoparticles, and $C_{\overline{\omega}}(IO)$ is the standard deviation in the size distribution of iron oxide nanoparticles, and in Relation 2, $D_\mu(Cap)$ is the average size of iron oxide nanocapsules, and $C_{\overline{\omega}}(Cap)$ is the standard deviation in the size distribution of iron oxide nanocapsules, and in Relation 3, $F(IO)$ is encapsulation efficiency which refers wt % of iron oxide nanoparticles encapsulated in the iron oxide nanocapsules, and in Relation 4, $D_\mu(IO)$ is defined as in Relation 1, and in Relation 5, $D_\mu(Cap)$ is defined as in Relation 2.)

As such, the size indicates a diameter, $D_\mu(IO)$ indicates an average diameter of iron oxide nanoparticles having a hydrophobic ligand attached thereto, the size distribution of iron oxide nanoparticles in $C_{\overline{\omega}}(IO)$ indicates the diameter distribution of iron oxide nanoparticles having a hydrophobic ligand attached thereto, and $F(IO)$ indicates an average amount of iron oxide nanoparticles encapsulated in the plurality of iron oxide nanocapsules.

As mentioned above, the iron oxide nanoparticles having a hydrophobic ligand attached thereto, encapsulated in the iron oxide nanocapsules according to the present invention, satisfy Relation 4. If the diameter of the iron oxide is less than 1 nm, the magnetization value is too low and T2 contrast enhancement is remarkably reduced, making it difficult to use it as a contrast agent. On the other hand, if the diameter exceeds 25 nm, the iron oxide nanoparticles have a high magnetization value, but may become ferromagnetic and residual magnetization may continue even under the condition of an external magnetic field being removed, and thus aggregation of the particles may be severe, making it unsuitable to use them as a contrast agent.

The hydrophobic ligand attached to the surface of the iron oxide nanoparticles functions to stabilize the surface of iron oxide nanoparticles. The hydrophobic ligand bound to the iron oxide nanoparticles includes one or more selected from among oleic acid, stearic acid, lauric acid, palmitic acid, octanoic acid, and decanoic acid.

In the iron oxide nanoparticles having a hydrophobic ligand attached thereto, the mass proportion of hydrophobic ligand is 5~60 wt %, particularly 10~40 wt %, and more particularly 20~30 wt %.

If the amount of hydrophobic ligand is less than 5 wt %, the surface of iron oxide nanoparticles is not sufficiently covered and thus aggregation and precipitation of iron oxide particles cannot be prevented, undesirably decreasing dispersibility in a solvent. On the other hand, if the amount of hydrophobic ligand exceeds 60 wt %, the encapsulation efficiency in capsules may remarkably decrease.

Also in the present invention, the iron oxide nanoparticles having a hydrophobic ligand attached thereto, encapsulated in the iron oxide nanocapsules, satisfy Relation 1. In Relation 1, $100 \cdot D_\mu(IO)/C_{\overline{\omega}}(IO)$ means the uniformity of iron oxide nanoparticles. The uniformity is defined as 100/Coefficient of Variance (C.V.), in which the coefficient of variance (C.V.) is defined as standard deviation/average value. Accordingly, the uniformity of iron oxide nanoparticles of Relation 1 is 100/C.V. of iron oxide nanoparticles, in which the C.V. of iron oxide nanoparticles is the standard deviation in the size distribution of iron oxide nanoparticles/ the average size of iron oxide nanoparticles.

When the uniformity of iron oxide nanoparticles satisfies Relation 1 in this way, the iron oxide nanoparticles encapsulated in the iron oxide nanocapsules may aggregate in a uniform size of 50 nm or more, thus increasing the relaxivity (R2).

More specifically, when the uniformity of iron oxide nanoparticles is 5 or more, iron oxide particles having constant solubility and only a desired size are used, and thus the encapsulation efficiency in capsules is increased thus enhancing relaxivity of capsules. On the other hand, if the uniformity is 5 or less, the proportion of nanoparticles different from the desired size may increase, undesirably deteriorating the contrast enhancement. Specifically, nanoparticles smaller than the desired size have a low magnetization, undesirably lowering the relaxivity of capsules. On the other hand, nanoparticles larger than the desired size have low dispersibility in a solvent thus reducing the encapsulation efficiency in capsules, so that aggregation effects may disappear, undesirably deteriorating the relaxivity.

The T2 relaxivity resulting from using 10 nm iron oxide nanoparticles having a uniformity of 10.1 obtained in Preparative Example 1 was 345.7 mM$^{-1}$ s$^{-1}$, and the nanocapsules obtained from mixture nanoparticles having a low uniformity of 2.8 comprising 10 nm iron oxide nanoparticles of Preparative Example 1 and 4 nm iron oxide nanoparticles of Preparative Example 2 exhibited a T2 relaxivity of 202.8 mM$^{-1}$ s$^{-1}$, from which the contrast enhancement can be seen to be considerably decreased.

As mentioned above, the iron oxide nanocapsules according to the present invention satisfy Relation 5. In the case where a contrast agent containing the iron oxide nanocapsules according to the present invention is injected into a blood vessel, the absorption, distribution, metabolism and elimination in vivo are greatly affected by the size of the iron oxide nanocapsules. The nanocapsules having a diameter of less than 50 nm may be in danger of a large amount of nanocapsules being distributed to lymph nodes rather than the desired tissue. On the other hand, if the diameter thereof exceeds 200 nm, the blood vessels may be blocked by such nanocapsules, and the absorption rate into liver tissue is low, making it unsuitable to use such nanocapsules as a contrast agent, in particular, a liver-specific contrast agent.

Also in the present invention, the iron oxide nanocapsules satisfy Relation 2. In Relation 2, $100*D_\mu(Cap)/C_{\overline{\omega}}(Cap)$ means the uniformity of iron oxide nanocapsules. Specifically, the uniformity of the iron oxide nanocapsules of Relation 2 is 100/C.V. of iron oxide nanocapsules, in which the C.V. of iron oxide nanocapsules is the standard deviation in the size distribution of iron oxide nanocapsules/the average size of the iron oxide nanocapsules.

When the uniformity of iron oxide nanocapsules satisfies Relation 2 in this way, the absorption by a tissue other than the desired tissue upon injection for MRI contrast purposes may be suppressed, and thus, the desired tissue may be observed in high contrast for the same injection amount.

As mentioned above, the iron oxide nanocapsules according to the present invention satisfy Relation 3. The iron oxide nanocapsules according to the present invention contain a large amount of iron oxide nanoparticles encapsulated therein, as in Relation 3. Even in the case of a contrast agent comprising the iron oxide nanocapsules in a low concentration according to the present invention, very high contrast enhancement may result. In particular, the concentration of iron oxide nanocapsules contained in the contrast agent may be drastically reduced compared to 0.42 mg Fe/Kg which is the human dose of a commercially available contrast agent. As the iron oxide nanocapsules according to the present invention satisfy Relation 3, the price of a contrast agent may be reduced, and also the side effects and shock caused by the injection of the contrast agent into the human body may be prevented.

More specifically, the iron oxide nanocapsules further satisfy Relations 6 and 7 below.

$$10 \leq 100*D_\mu(IO)/C_{\overline{\omega}}(IO) \quad \text{[Relation 6]}$$

$$5 \leq 100*D_\mu(Cap)/C_{\overline{\omega}}(Cap) \quad \text{[Relation 7]}$$

(in Relation 6, $D_\mu(IO)$ and $C_{\overline{\omega}}(IO)$ are defined as in Relation 1, and in Relation 7, $D_\mu(Cap)$ and $C_{\overline{\omega}}(Cap)$ are defined as in Relation 2.)

As the uniformity of iron oxide nanoparticles encapsulated in the iron oxide nanocapsules according to the present invention satisfies Relation 6, a plurality of iron oxide nanoparticles encapsulated in the nanocapsules are more uniformly aggregated. Furthermore, as the uniformity of iron oxide nanocapsules satisfies Relation 7, the absorption of nanocapsules by tissue other than the desired tissue to thus decrease contrast enhancement may be more effectively prevented. As such, in Relations 6 or 7, the uniformity of the iron oxide nanoparticles is actually 1000 or less, and the uniformity of the nanocapsules is 1000 or less.

More specifically, the iron oxide nanocapsules according to the present invention satisfy Relation 8.

$$7 \text{ wt \%} \leq F(IO) \leq 35 \text{ wt \%} \quad \text{[Relation 8]}$$

(in Relation 8, F(IO) is defined as in Relation 3.)

As such, a high encapsulation efficiency of the iron oxide nanoparticles is achieved by mixing a dispersion solution of iron oxide nanoparticles comprising 0.1~20 wt %, preferably 0.5~8 wt % of iron oxide nanoparticles dispersed in an organic solvent and 0.1~20 wt %, preferably 0.5~8 wt %, more preferably 0.5~4 wt % of a biodegradable polymer dissolved therein with an aqueous surfactant solution and emulsifying the mixture, thus preparing an emulsion, followed by adding water to the emulsion, thus manufacturing the iron oxide nanocapsules.

In the present invention, the encapsulation material of iron oxide nanoparticles according to the present invention includes the biodegradable polymer. The biodegradable polymer may be used without limitation so long as it is harmless to the human body and has high biocompatibility, and examples thereof include polylactide (PLA), polyglycolide (PGA), poly(lactide-co-glycolide) (PLGA) as a copolymer thereof, and mixtures thereof.

In particular, PLGA which is harmless to the human body, and has biostability and biocompatibility has been approved as an injection agent by the FDA, and thorough research into PLGA as a delivery medium for a drug that is hydrophobic and does not dissolve in water is ongoing. Also its decomposition rate in vivo may be adjusted depending on the ratio of PLA and PGA, and thus PLGA is an encapsulation material suitable for collecting the iron oxide nanoparticles having a hydrophobic ligand attached thereto so as to deliver them into a living body.

The molecular weight of the biodegradable polymer (Mw) is 1,000~250,000, preferably 2,000~100,000, and more preferably 5,000~20,000.

In the present invention, the encapsulation material of iron oxide nanoparticles includes the surfactant, in which the surfactant includes one or more selected from among sodium lauryl sulfate, polyvinylalcohol, poloxamer, polysorbate, and alkyldiphenyloxide disulfonate. The surfactant contained in the encapsulation material functions to form an emulsion of organic solution of polymer-iron oxide nanoparticles and to diffuse the nano-sized particles. For biostability and dispersion stability of iron oxide nanocapsules, the weight ratio of biodegradable polymer to surfactant contained in the encapsulation material may be set to 100 (biodegradable polymer):10~10000(surfactant), preferably 100(biodegradable polymer):100~1000(surfactant).

In addition, the present invention provides an MRI T2 contrast agent containing the iron oxide nanocapsules, in particular, an MRI T2 liver-specific contrast agent containing the iron oxide nanocapsules.

The MRI T2 contrast agent according to the present invention includes iron oxide nanocapsules in which superparamagnetic iron oxide nanoparticles having the above size and distribution are encapsulated in a very high encapsulation efficiency, and has very high T2 contrast effects at low concentration. Also, the iron oxide nanocapsules, whose size and distribution are controlled, are effectively distributed in the desired tissue, thus enhancing contrast and preventing side effects in the human body. In the contrast agent containing the iron oxide nanocapsules according to the present invention, the desired tissue is the liver.

Below, the method of manufacturing iron oxide nanocapsules according to the present invention is described. As results of repeating many tests of the manufacturing method according to first and second aspects by the present applicant, the main factor for controlling the encapsulation efficiency of iron oxide nanoparticles, the main factor for controlling the aggregation of encapsulated iron oxide nanoparticles, and the main factor for controlling the size and distribution of iron oxide nanocapsules were deduced.

The method of manufacturing iron oxide nanocapsules according to the present invention adopts an emulsification-diffusion method, and includes the following methods (I) (II) according to first and second aspects.

Specifically, the method (I) of manufacturing iron oxide nanocapsules according to the present invention includes a1) dissolving a biodegradable polymer in a polar organic solvent, adding iron oxide nanoparticles having a hydrophobic ligand attached thereto to the polar organic solvent, and performing ultrasonication, thus preparing a dispersion solution of iron oxide nanoparticles; b) mixing the dispersion solution of iron oxide nanoparticles with an aqueous surfactant solution, and performing emulsification, thus preparing an emulsion; and c) adding water to the emulsion to induce diffusion, thus manufacturing iron oxide nanocapsules.

More specifically, according to the first aspect of the present invention, the biodegradable polymer is first dissolved in the polar organic solvent (first solvent) that provides an oil phase in the emulsification-diffusion method and is partially water-miscible, thus preparing a biodegradable polymer solution in which the polarity of the organic solvent is weakened, after which the iron oxide nanoparticles having a hydrophobic ligand attached thereto are added to the biodegradable polymer solution, followed by performing ultrasonication, thus preparing the dispersion solution of iron oxide nanoparticles.

Subsequently, a surfactant is dissolved in water that provides a water phase in the emulsification-diffusion method, thus preparing the aqueous surfactant solution which is then mixed with the dispersion solution of iron oxide nanoparticles, and the mixture is emulsified using a homogenizer.

Subsequently, water is added to the emulsion thus prepared, so that the iron oxide-biodegradable polymer-surfactant of the emulsion is diffused into the water phase, thus manufacturing the iron oxide nanocapsules.

In addition, the method (II) of manufacturing iron oxide nanocapsules according to the present invention specifically includes a2) dissolving a biodegradable polymer in a polar organic solvent; a3) dispersing iron oxide nanoparticles having a hydrophobic ligand attached thereto in a non-polar organic solvent having a boiling point lower than that of the polar organic solvent; a4) mixing the polar organic solvent having the biodegradable polymer dissolved therein with the non-polar organic solvent having the iron oxide nanoparticles dispersed therein, and performing distillation to remove the non-polar organic solvent, thus preparing a dispersion solution of iron oxide nanoparticles; b) mixing the dispersion solution of iron oxide nanoparticles with an aqueous surfactant solution and performing emulsification, thus obtaining an emulsion; and c) adding water to the emulsion to perform diffusion, thus manufacturing iron oxide nanocapsules.

In the first aspect or the second aspect, the method may further include performing dialysis and lyophilization thus manufacturing iron oxide nanocapsule powder, after c).

The iron oxide nanoparticles satisfy Relations 1 and 4, and the iron oxide nanoparticles used to prepare the dispersion solution of iron oxide nanoparticles are iron oxide nanoparticles having a hydrophobic ligand attached to the surface thereof obtained by thermally decomposing an iron complex in which a hydrophobic organic acid group as a ligand is bound to iron as a central atom.

The size and distribution of iron oxide nanocapsules are controlled by stirring that is carried out upon both emulsification and diffusion. Specifically, in order to manufacture iron oxide nanocapsules according to the present invention, stirring is performed at 8000 rpm or more, preferably 8000~26000 rpm upon emulsification, and stirring is conducted at 100 rpm or more, preferably 100~2500 rpm upon diffusion.

More specifically, upon emulsification using a homogenizer, stirring is carried out at 8,000 rpm or more, preferably 8000~26000 rpm for 2~15 minutes. If the stirring time is less than 2 minutes, the mixture solution may not be sufficiently stirred. On the other hand, if the stirring time is longer than 15 minutes, the capsules may not be efficiently diffused due to the hardening of a polymer coming into contact with water. Also if the stirring rate is less than 8,000 rpm, the size of droplets of the initial emulsion may increase and thus the size of the final capsules may be 300 nm or more even after the diffusion process.

In the manufacturing method according to the present invention, the diffusion process is carried out in such a manner that water is added to the emulsion so that the solvent and the iron oxide-polymer-surfactant particles are diffused, thus manufacturing the nanocapsules. When water is added to the emulsion, the emulsion is instantly supersaturated while the amount of water therearound increases, and small organic solvent lumps having a size of hundreds of nm are separated from the surface of the emulsion, finally forming the nanocapsules. The volume of water added in the diffusion process may be 2 to 15 times that of the emulsion prepared in the emulsion preparing process.

As such, the stirring rate upon diffusion with the addition of water may be 100 rpm or more, preferably 100~2500 rpm. If the stirring rate is less than 100 rpm, shear force is small and thus the conditions around the emulsion cannot be rapidly changed, undesirably increasing the average size of capsules and the size uniformity.

In the manufacturing method according to the second aspect of the present invention, the size and distribution of iron oxide nanocapsules are controlled by the amount of non-polar organic solvent that remains after distillation at a4). Distilling temperature may be higher than the boiling point of the non-polar organic solvent and may be lower than the boiling point of the polar organic solvent.

The non-polar organic solvent having a low boiling point is selectively removed by the above distillation. As such, by adjusting the distillation time, the amount of remaining non-polar organic solvent may be controlled. The amount of non-polar organic solvent that remains in the above polar organic solvent has an influence on the emulsion size and size distribution upon emulsification, and also on the diffusion driving force of iron oxide-polymer-surfactant particles upon diffusion, so that the size and size distribution of the nanocapsules are controlled.

In order to control the size and size distribution of the nanocapsules, the distillation at a4) is performed so that the volume ratio of polar organic solvent to non-polar organic solvent is 100:1 or less, actually 100:0.001~1. As such, while the volume ratio of polar organic solvent to non-polar organic solvent is controlled by the distillation, the stirring conditions upon emulsification and diffusion should also be satisfied.

In the manufacturing method according to the present invention (including the first aspect or the second aspect), the amount of iron oxide nanoparticles encapsulated in the iron oxide nanocapsules is controlled by the concentration of iron oxide nanoparticles and the concentration of biodegradable polymer in the dispersion solution of nanoparticles. Furthermore, the aggregation of iron oxide nanoparticles encapsulated in the nanocapsules is controlled by the concentration of iron oxide nanoparticles and the concentration of biodegradable polymer, contained in the dispersion solution of iron oxide nanoparticles. To manufacture the iron oxide nanocapsules according to the present invention, the dispersion solution of nanoparticles may include 0.1~20 wt %, preferably 0.5~8 wt % of iron oxide nanoparticles and 0.1~20 wt %, preferably 0.5~8 wt %, more preferably 0.5~4 wt % of biodegradable polymer to manufacture the iron oxide nanocapsules satisfying Relation 8.

The polar organic solvent is an organic solvent that is partially water-miscible and includes one or more selected from among ethylacetate, methylene chloride, dimethyl sulfoxide, propylene carbonate, and benzylalcohol.

In the second aspect of the present invention, the non-polar organic solvent is an organic solvent that has a polarity lower than that of the polar organic solvent, and includes one or more selected from among hexane, heptane, pentane, and octane.

The biodegradable polymer includes one or more selected from among polylactide, polyglycolide, and poly(lactide-co-glycolide, and the surfactant includes one or more selected from among sodium lauryl sulfate, polyvinylalcohol, poloxamer, polysorbate, and alkyldiphenyloxide disulfonate. As such, the concentration of aqueous surfactant solution is 1~10 wt %, and the weight ratio of biodegradable polymer to surfactant in the above emulsion is 100(biodegradable polymer):10~10000 (surfactant), preferably 100(biodegradable polymer):100~1000 (surfactant).

Advantageous Effects

According to the present invention, low encapsulation efficiency problems of a conventional emulsificaion-diffusion method can be solved, so that iron oxide nanoparticles having a hydrophobic ligand attached thereto can be encapsulated in polymer/surfactant nanocapsules at a very high encapsulation efficiency. In particular, in the case of the typical emulsificaion-diffusion method, when the encapsulation efficiency is 5 wt % or more, the average size of nanocapsules increases due to aggregation of iron oxide nanoparticles, and the size uniformity decreases, and thus the stability of nanocapsules in the aqueous solution is considerably reduced and precipitation occurs rapidly within ones of hours. However, in the present invention, even when the encapsulation efficiency is increased, the average size of the resulting nanocapsules can be controlled to 200 nm or less, with a size uniformity of 5 or more, and also the stability of the nanocapsules in an aqueous solution is greatly increased, and thus precipitation does not occur in less than ones of days.

Upon applying the nanocapsules according to the present invention to an MRI contrast agent, the aggregation effects of iron oxide nanoparticles in the capsules can be increased, whereby the contrast enhancement can be raised to the level that can exceed the contrast enhancement of conventional contrast agents. Furthermore, the size of the capsules can be simultaneously adjusted, and thus upon use as a contrast agent, the absorption and distribution to desired tissue can be reproducibly adjusted. Moreover, the size uniformity is high thus preventing the formation of large particles of 200 nm or more. Thereby, such side effects as the blocking of capillary vessels can be prevented in vivo, thus manifesting very high safety. Also, a high encapsulation efficiency of the iron oxide nanoparticles can decrease the total concentration of contrast agent, so that the osmotic pressure and the viscosity can be reduced, whereby safety and convenience of patients who are administered with a contrast agent can greatly increase.

DESCRIPTION OF DRAWINGS

The above and other objects, features and advantages of the present invention will become apparent from the following description of preferred embodiments given in conjunction with the accompanying drawings, in which:

FIG. 1 is a transmission electron microscope (TEM) image showing iron oxide nanoparticles having a hydrophobic ligand attached thereto, obtained in Preparative Example 1;

FIG. 2 is a TEM image showing iron oxide nanoparticles having a hydrophobic ligand attached thereto, obtained in Preparative Example 2;

FIG. 3 is of optical photographs showing PLGA-iron oxide nanocapsules of Example 1 dispersed in an aqueous phase, before and after encapsulation;

FIG. 4 is a TEM image showing the PLGA-iron oxide nanocapsules of Example 1;

FIG. 5 is of a graph and a magnetic resonance image showing the contrast enhancement in vitro of the PLGA-iron oxide nanocapsules of Example 1, compared to the results of using a commercially available contrast agent Feridex;

FIG. 6 is of magnetic resonance images showing the contrast enhancement in vivo of the PLGA-iron oxide nanocapsules of Example 1, in which pre, 1 HR and 2 HR indicate measurements before injection, 1 hour after injection, and 2 hours after injection;

FIG. 7 is of graphs showing the dose of the PLGA-iron oxide nanocapsules of Example 1 versus the contrast enhancement in vivo, compared to the results of using a commercially available contrast agent Feridex;

FIG. 8 is a graph showing the encapsulation efficiency of the PLGA-iron oxide nanocapsules of Example 1 versus the contrast enhancement in vivo, compared to the results of using a commercially available contrast agent Resovist;

FIG. 9 is a graph showing the size of the PLGA-iron oxide nanocapsules of Example 1 versus the contrast enhancement in vivo, compared to the results of using a commercially available contrast agent Resovist;

FIG. 10 is of graphs showing the cell viability depending on the concentration and incubation time of the PLGA-iron oxide nanocapsules of Example 1, compared to the results of using a commercially available contrast agent Feridex;

FIG. 11 is a TEM image showing PLGA-iron oxide nanocapsules of Comparative Example 1 having a uniformity of iron oxide nanoparticles of 2.8, obtained in Comparative Example 1;

FIG. 12 is a TEM image showing PLGA-iron oxide nanocapsules in which the encapsulation efficiency of iron oxide nanoparticles is 0.5 wt % or less, obtained in Comparative Example 2; and FIG. 13 is of images and a graph showing the contrast enhancement in vivo of PLGA-iron oxide nanocapsules having a size of 200 nm or more, obtained in Comparative Example 3.

BEST MODE

Hereinafter, the present invention will be described in detail based on the following examples and comparative examples, but is not limited to such examples.

Furthermore, the fundamental concepts and embodiments of the present invention will be able to be easily modified or changed by those skilled in the art.

Preparative Example 1

Mass Production of Monodispersed 10 nm Iron Oxide Nanoparticles Having Oleate Attached Thereto 10.8 g of iron oxide and 36.5 g of sodium oleate were dissolved in a solvent mixture comprising 80 ml of ethanol, 60 ml of distilled water, and 140 ml of hexane, and the obtained solution was heated to 57° C. and maintained at the same temperature for 1 hour. In this procedure, initial orange color of water phase became clear, and an initial transparent organic phase turned to a red color, after which the upper organic layer containing iron oleate complex was separated, and hexane was then evaporated, thus obtaining a viscous liquid. 36 g of the iron oleate complex (obtained a viscous liquid) was added to a mixture comprising 200 g of octadecene and 5.7 g of oleic acid.

The mixture thus obtained was heated to 70° C. from room temperature at a heating rate of 2.5° C./min in a vacuum, and maintained at the same temperature for 1 hour so that the remaining solvent and moisture were removed leaving behind the reaction material. Thereafter, the reaction material was heated to 320° C. at a rate of 2.5° C./min in a nitrogen atmosphere, and maintained at the same temperature for 1 hour and aged. In this procedure, vigorous reaction occurred, and the initial red solution turned to a black brown color, meaning that the iron oleate complex was completely decomposed and iron oxide nanoparticles were produced. After the reaction completed, when the temperature arrived at an automatic ignition temperature or less (150° C.) via natural cooling, air was fed so that oxidation was carried out.

The solution containing nanoparticles thus formed was cooled to room temperature, and a mixture solution comprising hexane and acetone at a volume ratio of was added in an amount corresponding to three times the volume of a stock solution, thus forming black precipitates, which were then separated using centrifugation (rpm=2,000).

The supernatant was decanted. This washing process was repeated at least two times, and the hexane and acetone contained in the remainder were removed using drying, and the product thus obtained was iron oxide nanoparticles to be easily re-dispersed in hexane. FIG. 1 is a TEM image showing the finally produced iron oxide nanoparticles, having an average size of 10 nm and a size uniformity of 10.1.

Preparative Example 2

Mass Production of Monodispersed 4 nm Iron Oxide Nanoparticles Having Oleate Attached Thereto Iron oxide nanoparticles were mass synthesized in the same manner as in Preparative Example 1, with the exception that 100 g of hexadecane was used as the solvent, and the final heating temperature was 280° C.

The nanoparticles thus obtained were easily re-dispersed in a non-polar organic solvent such as hexane or toluene. FIG. 2 is a TEM image showing the final iron oxide nanoparticles, having an average size of 4 nm and a size uniformity of 6.15.

Example 1

Manufacture of PLGA-Iron Oxide Nanocapsules Using Changes in Solubility of Biodegradable Polymer Solution 200 mg of PLGA having a carboxyl terminal group and a molecular weight (Mw) of 5,000 was added to 10 ml of ethylacetate and stirred for 10 minutes to completely dissolve it. 200 mg of the monodispersed iron oxide nanoparticles of Preparative Example 1 was added to the above solution and ultra-sonicated at 45° C. for 60 minutes, thus preparing a dispersion solution of iron oxide nanoparticles. When the iron oxide nanoparticles were not completely dispersed in the solvent, an opaque brown color was evident, and most of them precipitated within 5 minutes. On the other hand, in the case where the iron oxide nanoparticles were completely dispersed using ultrasonication, there was a deep transparent black color and precipitation did not occur for ones of days or longer.

10 ml of the dispersion solution of iron oxide nanoparticles thus prepared was mixed with 20 ml of a 5 wt % aqueous solution of Pluronic F-127 (P2443, Sigma, Cas No. 9003-11-6) and emulsified for 7 minutes at 20,000 rpm using a homogenizer. While the emulsified solution was immediately placed in a 200 ml beaker and stirred at 500 rpm, 100 ml of distilled water was added thereto at one time and stirring was performed for 20 minutes. The prepared solution was then placed in a dialysis membrane and stirred for two days, so that the reaction remainder was removed, after which the resultant product was frozen at −20° C., and lyophilized, thus obtaining nanocapsule powder. FIG. 3 shows images of the above PLGA-iron oxide nanocapsules dispersed in water phase. Before encapsulation the iron oxide nanoparticles having oleate attached thereto were distributed in only the hexane layer, whereas after encapsulation the nanocapsules stabilized with PLGA and Pluronic F-127 were stably distributed in the water layer and observed to be stable without precipitation for ones of weeks.

FIG. 4 is a TEM image showing that the formation of the above PLGA-iron oxide nanocapsules was very uniform, having an average size of 111.6 nm and a size uniformity of 12.5, in which the iron oxide nanoparticles were observed to be uniformly distributed in an encapsulation efficiency of 10.3 wt % in the capsules.

Example 2

Manufacture of PLGA-Iron Oxide Nanocapsules Using Non-Polar Organic Solvent and Distillation 200 mg of PLGA having a carboxyl terminal group and a molecular weight of 20,000 was added to 150 ml of ethylacetate and stirred for 10 minutes to completely dissolve it, thus preparing a first solution. 200 mg of the monodispersed iron oxide nanoparticles of Preparative Example 1 were added to 100 ml of hexane (a non-polar organic solvent) and ultra-sonicated for 1 hour to completely disperse them, thus preparing a second solution. The first solution and the second solution were mixed together and stirred for 30 minutes, and two solutions were observed to be completely mixed without phase separation.

The mixture solution comprising the first solution and the second solution was heated to 72° C. higher than the boiling point of hexane and lower than the boiling point of ethylacetate and distilled until the amount of the remaining solution was about 10 ml, thus preparing a dispersion solution of iron oxide nanoparticles. Although hexane having an azeotropic point with ethylacetate was distilled together, its evaporation rate was faster, and thus, in the case where 10 ml of the final solution remained, the remaining hexane was 1 vol % or less, and the iron oxide nanoparticles were seen to be dispersed in the final ethylacetate left behind.

10 ml of the prepared dispersion solution of iron oxide nanoparticles was mixed with 20 ml of 5 wt % aqueous solution of Pluronic F-127 and emulsified for 7 minutes at 20,000 rpm using a homogenizer. While the emulsified solution was immediately placed in a 200 ml beaker and stirred at 500 rpm, 100 ml of distilled water was added thereto at one time and stirring was performed for 20 minutes. The prepared solution was then placed in a dialysis membrane and stirred for two days, so that the reaction remainder was removed, after which the resultant product was frozen at −20° C., and lyophilized, thus obtaining nanocapsule powder.

The PLGA-iron oxide nanocapsules thus manufactured contained iron oxide nanoparticles encapsulated in a very high encapsulation efficiency of 10.3 wt % and had an average size of 178.4 nm and a size uniformity of 7.2, and were regarded as very uniform.

Example 3

Manufacture of PLGA-Iron Oxide Nanocapsules Having High Encapsulation Efficiency Nanocapsules were manufactured in the same manner as in Example 1, with the exception that 40 mg of PLGA, 3 ml of ethylacetate, 200 mg of iron oxide nanoparticles, and 6 ml of 5 wt % aqueous solution of Pluronic F-127 were used, and a stirring rate upon emulsification was 26,000 rpm.

The PLGA-iron oxide nanocapsules thus manufactured had an average size of 168.9 nm and a size uniformity of 6.4, and were regarded as uniform. In particular, the encapsulation efficiency of iron oxide nanoparticles was 27.4 wt % which was much higher than 7 wt % that was considered to be a threshold due to aggregation of iron oxide nanoparticles in a conventional emulsificaion-diffusion method.

Example 4

Manufacture of PLGA-Iron Oxide Nanocapsules Having Small Average Size

Nanocapsules were manufactured in the same manner as in Example 1, with the exception that 40 mg of PLGA, 3 ml of ethylacetate, 40 mg of iron oxide nanoparticles, and 6 ml of 5 wt % aqueous solution of Pluronic F-127 were used, and a stirring rate upon emulsification was 26,000 rpm.

The PLGA-iron oxide nanocapsules thus manufactured contained the iron oxide nanoparticles encapsulated in a very high encapsulation efficiency of 8.8 wt % and had an average size of 90.9 nm and a size uniformity of 7.2, and were regarded as very small and uniform.

Example 5

Measurement of Magnetic Resonance Relaxivity In Vitro of Nanocapsules

In order to evaluate the usability of the PLGA-iron oxide nanocapsules of Example 1 as an MRI T2 liver-specific contrast agent, T2 relaxivity in vitro was measured using a BGA12 gradient coil in a 4.7 T magnetic resonance imaging system (Biospec 47/40, Bruker Biospin MRI GmbH). The iron concentration of iron oxide-PLGA nanocapsule powder was analyzed via ICP-AES, and dispersed in a concentration of 1~4 μg Fe/ml in a solution of 0.01M PBS (Phosphate Buffered Saline, pH 7.4). The first solution was diluted by half to prepare a total of five kinds of samples, which were then placed in 250 μl tubes to measure T2 relaxation time at one time. The measurement of T2 relaxation time was performed using MSME (Multi Slice Multi Echo sequence) pulse sequence. Specific parameters are as follows.
TR(repetition time)=10,000 ms, TE(echo time)=8-2048 ms (256 times at intervals of 8 ms), FOV=60×40 mm, Resolution=0.234×0.156 mm/pixel, slice thickness=1 mm, number of acquisition=1, Matrix size=128×128

FIG. 5 is of a graph and a magnetic resonance image showing the contrast enhancement in vitro of the PLGA-iron oxide nanocapsules of Example 1, from which the contrast enhancement of the capsules manufactured using the method according to the present invention can be seen to be much higher than that of the commercially available contrast agent.

Example 6

Measurement of Magnetic Resonance Relaxivity In Vivo of Nanocapsules

In order to evaluate the usability of the PLGA-iron oxide nanocapsules of Example 1 as an MRI T2 liver-specific contrast agent, T2 relaxivity in vivo was measured using BGA12 gradient coil in a 4.7 T magnetic resonance imaging system (Biospec 47/40, Bruker Biospin MRI GmbH).

The MR test in vivo was carried out using a five-week-old male Balb/c mouse weighing about 20~25 g. The mouse was anesthetized and then placed horizontally in an MRI apparatus to observe the coronal plane, and in order to observe the liver tissue of the same plane, the mouse was subjected to inhalation anesthesia for the total test time so that the mouse barely moved. The iron concentration of iron oxide-PLGA nanocapsule powder was analyzed using ICP-AES, and dispersed in 0.01M PBS solution, after which 200 μl of the PLGA-iron oxide nanocapsule solution was injected at one time through the tail vein of the mouse, and the final dosage of the solution was set to 1 mg Fe/kg in consideration of the body weight of the mouse. The T2 relaxation time was measured using RARE (Rapid Acquisition with Refocused Echoes) pulse sequence, and specific parameters thereof are as follows.

TR(repetition time)=3,500 ms, TE(echo time)=36 ms, FOV=60×40 mm, Resolution=0.234×0.156 mm/pixel, slice thickness=1 mm, number of acquisition=4, Matrix size=256×256

In order to quantitatively measure T2 decay effects of PLGA-iron oxide nanocapsules, a cross-section of the liver tissue was selected and the entire liver portion was adopted as a ROI (Region of Interests) and signal intensity (SI) thereof was analyzed. In order to maximize the reliability of the obtained SI, a 1 wt % agarose solution was placed in a 200 μl tube, cooled, solidified, fixed around the abdominal cavity of the mouse, and used as the control. The T2 decay effect of PLGA-iron oxide nanocapsules was calculated from Equation 1 below and graphed.

$$T2 \text{ decay effect } (\Delta R2) = 100 \ast [1 - (SNR)_\tau/(SNR)_0]$$
(SNR: Signal to Noise Ratio)　　　　(Equation 1)

$(SNR)_\tau = (SI \text{ of } ROI)_\tau/(SI \text{ of Agarose})_\tau$
$(SNR)_0 = (SI \text{ of } ROI)_0/(SI \text{ of Agarose})_0$ In Equation 1, SI of ROI means the signal intensity in the liver corresponding to the region of interest, and SI of agarose means the signal intensity of agarose used as a control for the liver tissue, t means the signal intensity at t time after adding the contrast agent, and 0 means the signal intensity just before adding the contrast agent.

The contrast enhancement results of the PLGA-iron oxide nanocapsules of Example 1 and the commercially available contrast agent are compared in FIG. 4. The maximum T2 decay effect ($\Delta R2_{\mu\alpha\xi}$) of commercially available contrast agent was about 58%, whereas the PLGA-iron oxide nanocapsules according to the present invention exhibited a maximum T2 decay effect of about 73%, which was much higher than that of the commercially available contrast agent. Even when the inventive nanocapsules were used in a small amount, the diseased portion of the liver could be accurately diagnosed.

FIG. 6 is of magnetic resonance images showing the contrast enhancement in vivo of the PLGA-iron oxide nanocapsules of Example 1, in which the contrast enhancement in vivo of the inventive capsules can be seen to be much higher than that of the commercially available contrast agent.

FIG. 7 is of graphs showing the dose of the PLGA-iron oxide nanocapsules of Example 1 versus the contrast enhancement in vivo, in which the contrast enhancement in vivo of the inventive capsules is adjusted depending on the dose and is higher over the entire dose range compared to when using the commercially available contrast agent. In particular, the contrast enhancement thereof can be observed to be much higher compared to using 0.42 mg Fe/kg corresponding to the human dose of the commercially available contrast agent.

FIG. 8 is a graph showing the encapsulation efficiency of the PLGA-iron oxide nanocapsules of Example 1 versus the contrast enhancement in vivo, in which the contrast enhancement in vivo of the inventive capsules can be adjusted depending on the encapsulation efficiency. In particular, when the encapsulation efficiency of iron oxide nanoparticles is 19~27 wt %, the contrast enhancement can be observed to be higher than when using capsules having an encapsulation efficiency of 11 wt % or less.

FIG. 9 is a graph showing the size of the PLGA-iron oxide nanocapsules of Example 1 versus the contrast enhancement in vivo, in which the contrast enhancement in vivo of the inventive capsules can be adjusted by the size of the capsules. In the case where the capsules have a small size of 100 nm or less, contrast enhancement is observed to increase, and thus the size of the capsules and the size uniformity are regarded as very important.

Example 7

Measurement of Cytotoxicity of Nanocapsules

In order to evaluate the cytotoxicity of the PLGA-iron oxide nanocapsules of Example 1, MTT [3-(4,5-dimethyl-thiazol-2-yl)-2,5-diphenyl-2H-tetrazolium bromide)] assay was performed as a cell cytotoxicity test. The test was performed using HEK293 cell as the human kidney cell line and HepG2 cell as the liver cell line, and both of the two cell lines were adherent cells propagating in a state of attached to the surface of test vessel, and were inoculated in a density of $1\times10^5$ in a 96-well plate.

The cells were incubated for 24 hours after which the culture medium was removed, and the PLGA-iron oxide nanocapsules having a maximum concentration of 9762 ppm were diluted by half up to 19 ppm to prepare a total of nine kinds of solutions, 12.5 μl of each of which was added along with 87.5 μl of the culture medium to each well. Respective wells were incubated for 24 hours, and the culture medium was removed, 20 μl of MTT solution was added thereto, and incubation was carried out for 4 hours. Finally, 100 μl of a solubilization solution was added thereto and incubated, after which absorbance at 550 nm was measured, thus determining the cell viability.

As shown in FIG. 10, regardless of the concentration of PLGA-iron oxide nanocapsules of Example 1 and the incubation time, the viability was high for the entire cell line, and no cell toxicity was observed even at a concentration at least 300 times the use concentration of contrast agent comprising the PLGA-iron oxide nanocapsules according to the present invention.

Comparative Example 1

PLGA-Iron Oxide Nanocapsules Having Uniformity of Iron Oxide Nanoparticles of 10 or Less Using 10 ml of a solution of iron oxide nanoparticles prepared in the same manner as in Example 1 with the exception that 100 mg of 4 nm iron oxide nanoparticles and 100 mg of 10 nm iron oxide nanoparticles were mixed, the same procedures as in Example 3 were performed, thus manufacturing nanocapsules having a size uniformity of iron oxide nanoparticles of 2.8.

FIG. 11 is a TEM image showing the PLGA-iron oxide nanocapsules having a uniformity of iron oxide nanoparticles of 2.8. The average size of the capsules comprising 25 wt % of iron oxide nanoparticles having an average size of 4 nm and 75 wt % of iron oxide nanoparticles having an average size of 10 nm encapsulated therein was 146 nm, and the size uniformity of the capsules was approximately uniform to the level of about 5.12. However, because of low uniformity of iron oxide nanoparticles, T2 relaxivity was measured to be 202.8 mM$^{-1}$ s$^{-1}$, which was much lower than 345.7 mM$^{-1}$ s$^{-1}$ when using only the 10 nm iron oxide nanoparticles.

Comparative Example 2

PLGA-Iron Oxide Nanocapsules Having Encapsulation Efficiency of 0.5 Wt % or Less Using 10 ml of a solution of iron oxide nanoparticles prepared in the same manner as in Example 1 with the exception that 4 mg of iron oxide nanoparticles was used, the same procedures as in Example 3 were performed, thus manufacturing nanocapsules.

FIG. 12 is a TEM image showing the PLGA-iron oxide nanocapsules having an encapsulation efficiency of iron oxide nanoparticles of 0.5 wt % or less. As results of encapsulating the iron oxide nanoparticles having an average size of 10 nm and a size uniformity of 10 or more, very uniform PLGA-iron oxide nanocapsules having an average size of 147.6 nm and a size uniformity of 20 were manufactured. However, the use thereof as a contrast agent is limited because of the proportion of iron oxide being too low.

Comparative Example 3

PLGA-Iron Oxide Nanocapsules Having Average Size of 200 nm or More

Nanocapsules were manufactured in the same manner as in Example 3 with the exception that 10 ml of the solution of iron oxide nanoparticles prepared in Example 1 was used, the stirring rate upon emulsification was 7,000 rpm. FIG. 13 is of an image and a graph showing the contrast enhancement in vivo of the PLGA-iron oxide nanocapsules having a size of 200 nm or more. As results of encapsulating iron oxide nanoparticles having an average size of 10 nm and a size uniformity of 10 or more, PLGA-iron oxide nanocapsules having an average size of 520.9 nm and a size uniformity of 2.2 were manufactured. The capsules were in the size ranging from 100 nm to ones of μm. In particular, PLGA-iron oxide nanocapsules having a size of 200 nm or more exhibited low T2 relaxivity and low distribution in the liver and thus the maximum T2 decay effect (A R2$_{\mu\alpha\xi}$) was only about 34%.

Although the preferred embodiments of the present invention have been disclosed for illustrative purposes, those skilled in the art will appreciate that various modifications, additions, and substitutions are possible, without departing from the scope and spirit of the invention as disclosed in the accompanying claims.

The invention claimed is:

1. Iron oxide nanocapsules, in which a plurality of iron oxide nanoparticles having an oleate ligand attached thereto are encapsulated in an encapsulation material including a biodegradable polymer and a surfactant, and which satisfy Relations 1, 2, 3, 4 and 5 below:

$$10 \leq 100 * D_m(IO)/C_v(IO) \quad \text{Relation 1}$$

$$2.5 \leq 100 * D_m(Cap)/C_v(Cap) \quad \text{Relation 2}$$

$$7 \text{ wt \%} \leq F(IO) \leq 35 \text{ wt \%} \quad \text{Relation 3}$$

$$1 \text{ nm} \leq D_m(IO) \leq 25 \text{ nm} \quad \text{Relation 4}$$

$$50 \text{ nm} \leq D_m(Cap) \leq 200 \text{ nm} \quad \text{Relation 5}$$

in which:
in Relation 1, $D_m(IO)$ is an average size of iron oxide nanoparticles, and $C_v(IO)$ is a standard deviation in size distribution of iron oxide nanoparticles, and
in Relation 2, $D_m(Cap)$ is an average size of iron oxide nanocapsules, and $C_v(Cap)$ is a standard deviation in size distribution of iron oxide nanocapsules, and
in Relation 3, F(IO) is encapsulation efficiency which refers wt % of iron oxide nanoparticles encapsulated in the iron oxide nanocapsules, and
in Relation 4, $D_m(IO)$ is defined as in Relation 1, and
in Relation 5, $D_m(Cap)$ is defined as in Relation 2.

2. The iron oxide nanocapsules of claim 1, which further satisfy Relation 7 below:

$$5 \leq 100 * D_m(Cap)/C_v(Cap) \quad \text{Relation 7}$$

in which, $D_m(Cap)$ and $C_v(Cap)$ are defined as in Relation 2.

3. The iron oxide nanocapsules of claim 1, which are manufactured by mixing a dispersion solution of iron oxide nanoparticles comprising 0.1~20 wt % of iron oxide nanoparticles dispersed in an organic solvent and 0.1~20 wt % of a biodegradable polymer dissolved therein with an aqueous surfactant solution and performing emulsification, thus preparing an emulsion, and adding water to the emulsion.

4. The iron oxide nanocapsules of claim 1, wherein the biodegradable polymer is one or more biodegradable polymers selected from polylactide, polyglycolide, and poly (lactide-co-glycolide).

5. The iron oxide nanocapsules of claim 4, wherein the surfactant is one or more surfactants selected from sodium lauryl sulfate, polyvinylalcohol, poloxamer, polysorbate, alkyldiphenyloxide disulfonate.

6. The iron oxide nanocapsules of claim 1, wherein the biodegradable polymer has a molecular weight of 1,000~250,000 g/mol.

7. An MRI (Magnetic Resonance Imaging) T2 contrast agent, comprising the iron oxide nanocapsules of claim 1.

8. An MRI T2 liver-specific contrast agent, comprising the iron oxide nanocapsules of claim 1.

9. The iron oxide nanocapsules of claim 1, wherein the surfactant is one or more surfactants selected from sodium lauryl sulfate, polyvinylalcohol, poloxamer, polysorbate, alkyldiphenyloxide disulfonate.

* * * * *